(12) United States Patent
Egermann et al.

(10) Patent No.: US 7,693,677 B2
(45) Date of Patent: Apr. 6, 2010

(54) METHOD OF CHARACTERIZING THE DISTRIBUTION OF THE ABSOLUTE PERMEABILITY OF A HETEROGENEOUS SAMPLE

(75) Inventors: Patrick Egermann, Rueil Malmaison (FR); Mickaele Le Ravalec, Rueil-Malmaison (FR); Amir Soltani, Courbevoie (FR)

(73) Assignee: Institut Francais du Petrole (FR)

( * ) Notice: Subject to any disclaimer, the term of this patent is extended or adjusted under 35 U.S.C. 154(b) by 168 days.

(21) Appl. No.: 11/948,316

(22) Filed: Nov. 30, 2007

(65) Prior Publication Data
US 2008/0134760 A1 Jun. 12, 2008

(30) Foreign Application Priority Data
Dec. 1, 2006 (FR) ................... 06 10581

(51) Int. Cl.
*G01N 15/08* (2006.01)
(52) U.S. Cl. ..................... 702/127
(58) Field of Classification Search ........... 702/127
See application file for complete search history.

(56) References Cited
U.S. PATENT DOCUMENTS

| | | | |
|---|---|---|---|
| 4,868,751 A | 9/1989 | Dogru et al. | |
| 5,146,086 A | 9/1992 | De et al. | |
| 2005/0168220 A1 | 8/2005 | Lenormand et al. | |
| 2005/0178189 A1 | 8/2005 | Lenormand et al. | |
| 2005/0229680 A1* | 10/2005 | Kfoury et al. | 73/38 |

FOREIGN PATENT DOCUMENTS

| | | |
|---|---|---|
| EP | 1 548 455 A1 | 6/2005 |
| FR | 2 863 052 | 6/2005 |
| WO | WO 03/071253 A2 | 8/2003 |

OTHER PUBLICATIONS

Lin Y. Hu and Mickaele Le Ravalec-Dupin: "An Improved Gradual Deformation Method for Reconciling Random and Gradient Searches in Stochastic Optimizations", Mathematical Geology, vol. 36, No. 6, Aug. 2004, pp. 703-719, XP002440346.

* cited by examiner

*Primary Examiner*—Tung S Lau
(74) *Attorney, Agent, or Firm*—Antonelli, Terry, Stout & Kraus, LLP.

(57) ABSTRACT

The invention relates to a method having applications for oil exploration and $CO_2$ storage of determining the three-dimensional distribution of the absolute permeability of a heterogeneous sample. The method includes: determining a 3D porosity map of the sample; carrying out a viscous miscible displacement experiment during which the evolution of the differential pressure on either side of the sample is determined; from this evolution, determining a 1D absolute permeability profile along the sample and constructing a first 3D permeability map from the 3D porosity map; estimating a simulated differential pressure by simulating numerically a viscous miscible test from the first permeability map and from the 1D permeability profile; determining the three-dimensional distribution of the absolute permeability of the sample by modifying at least once the first permeability map so as to minimize the difference between the simulated differential pressure and the differential pressure measured over the course of time.

8 Claims, 5 Drawing Sheets

METHOD OF CHARACTERIZING THE DISTRIBUTION OF THE ABSOLUTE PERMEABILITY OF A HETEROGENEOUS SAMPLE

BACKGROUND OF THE INVENTION

1. Field of the Invention

The present invention relates to the field of petrophysical measurements on rock samples. More particularly, the invention relates to processes for characterizing the three-dimensional distribution of the absolute permeability of a heterogeneous sample from a rock.

2. Description of the Invention

There are different known approaches for characterizing a three-dimensional (3D) permeability map of a rock sample.

Identification of a 3D Map Based on "Manual" Identification

This approach uses a tracer test, that is a miscible test but without viscosity contrast, to obtain a permeability map. This technique is described in the following documents:

Dabbouk, C., Ali, L., Williams, G., Beattie, G.: "*Waterflood in Vuggy Layer in a Middle East Reservoir-Displacement Physics Understood*", SPE 78530, Abu Dhabi International Petroleum Exhibition and Conference, 13-16 Oct. 2002.

Olivier, P., Cantegrel, L., Laveissière, J., Guillonneau, N.: "*Multiphase Flow Behaviour in Vugular Carbonates Using X-Ray*", SCA 2004-13, Society of Core Analysts Symposium, Abu Dhabi, 5-9 Oct. 2004.

One or more laws $K(\Phi)$ are used to deduce from a porosity map a permeability map used for simulation of the tracer experiment. These laws $K(\Phi)$ are then manually adjusted until good agreement with the experiment is obtained. The advantage of this approach is its simplicity. On the other hand, a major drawback is that there is a very large number of solutions to this problem. Manual calibration only gives access to a single solution.

Identification of a 3D Map Based on a "Mathematical" Inversion

This technique also uses tracer tests. According to this method, it is possible to monitor, by tomography for example, the displacement of a front at various times. From this information, the permeability map is the solution to a non-linear problem with known boundary conditions. This method is described in:

Zhan, L., Yortsos, Y. C.: "*A Direct Method for the Identification of the Permeability Field of an Anisotropic Porous Medium*", SPE 62976, Annual Technical Conference and Exhibition, Dallas, 1-4 Oct. 2000.

Insofar as the boundary conditions (permeability or pressure profile at the boundaries) and the porosity map are known, this technique leads to a single solution that is valid only when the permeability contrasts are low. Implementation of this technique therefore remains limited in practice because the boundary conditions are not always known. This method does not apply to very heterogeneous media.

1D Profile Based on a Viscous Displacement

Using a viscous displacement to obtain information on the 1D permeability profile was proposed by Fincham and Gouth:

Fincham, A., Gouth, F.: "*Improvements of Coreflood Design and Interpretation Using a New Software*", SCA 2000, Society of Core Analysts Symposium, Abu Dhabi, 9-12 Oct. 2000.

The authors interpret the differential pressure signal of a viscous oil injection at a high flow rate in an initially brine-saturated clump in order to determine the 1D oil permeability profile at $S_{wi}$. This technique enables better characterization of the "local" heterogeneity of the sample and thus to fine tune the interpretation of the experiments intended to determine the relative permeability curves. However, this approach does not obtain the absolute permeability values, whether in 1D or in 3D.

SUMMARY OF THE INVENTION

The present invention is a method for characterizing, in a fast, precise and non-destructive manner, the three-dimensional distribution of the absolute permeability of any heterogeneous sample.

The invention relates to a method of determining a three-dimensional distribution of the absolute permeability of a heterogeneous sample, from a three-dimensional porosity map of the sample, comprising:

carrying out at least one viscous miscible displacement experiment during which an evolution of the differential pressure $DP(t)_{mes}$ is determined on either side of the sample;

determining a 1D absolute permeability profile along the sample using the differential pressure evolution;

constructing a 3D permeability map ($K(\Phi)$) from a 3D porosity map;

estimating a simulated differential pressure $DP(t)_{sim}$ by simulating numerically a viscous miscible test from the first permeability map and the 1D permeability profile; and determining the three-dimensional distribution of the absolute permeability of the sample by modifying at least once the first permeability map so as to minimize the difference between the simulated differential pressure $DP(t)_{sim}$ and the differential pressure measured over the course of time $DP(t)_{mes}$.

The porosity map can be determined from non-destructive static measurements.

The porosity map can be determined from X-ray measurements using fluids of different densities saturating said sample.

The porosity map can be determined from nuclear magnetic resonance measurements.

The first permeability map ($K(\Phi)$) can be determined from co-simulations.

The first permeability map ($K(\Phi)$) can be determined from at least one deterministic relation between the porosity and the permeability.

The first permeability map can be modified by applying a gradual deformation method.

A concentration profile or 3D concentration maps can also be determined at different times and compared with equivalent simulated responses $C_{sim}$.

BRIEF DESCRIPTION OF THE DRAWINGS

Other features and advantages of the method according to the invention will be clear from reading the description hereafter of embodiments given by way of non limitative example, with reference to the accompanying figures wherein.

DETAILED DESCRIPTION

The method according to the invention is based on an integrated approach combining the acquisition of fast experimental data, non-destructive for the sample, and the interpretation by means of a dedicated digital tool allowing access to the 3D absolute permeability map. According to the method, two types of experimental measurements are necessary:

Static measurement of a 3D porosity map of the sample:

This map can be calculated for example from X-ray measurements RX obtained with fluids of different densities saturating the porous medium. Other techniques such as NMR tomography also allow obtaining the porosity map. The local porosity value can then be calculated in a deterministic manner using the attenuation difference between the signals (NMR and/or X) obtained under the two saturation conditions, that is for the dry sample and the saturated sample. Such a method is described for example in the following document: Maloney, D. R., Wegener, D. C. "*Significance Absorption Coefficients When Determining In Situ Saturations by Linear X-ray Scans,*" International Symposium of the Society of Core Analysts, Socorro, USA, 2000;

A measurement based on at least one miscible displacement:

This displacement is carried out using an injection fluid that is more viscous than the fluid in place (viscosity ratio above 50 cP for example). It can be advantageous to carry out the tests by injecting the viscous fluid in both directions so as to fine tune the precision as regards interpretation of the results in terms of permeability. This measurement can be the difference between the pressures measured on either side of the sample.

The method then comprises a stage of interpretation of the results, which is carried out in two distinct stages. The first stage allows obtaining a 1D absolute permeability profile along the sample using the differential pressure evolution measured during the viscous miscible displacement tests. This 1D permeability profile is used in the second interpretation stage in combination with a 3D porosity map to obtain a 3D permeability map.

Experimental Implementation

1—Determination of a Three-Dimensional Porosity Map of the Sample

Many techniques allowing acquisition of a 3D porosity map are known. The following document can for example be referred to:

Maloney, D. R., Wegener, D.C. "*Significance Absorption Coefficients When Determining In Situ Saturations by Linear X-ray Scans,*" International Symposium of the Society of Core Analysts, Socorro, USA, 2000.

2—Viscous Miscible Displacements

Figure 1:
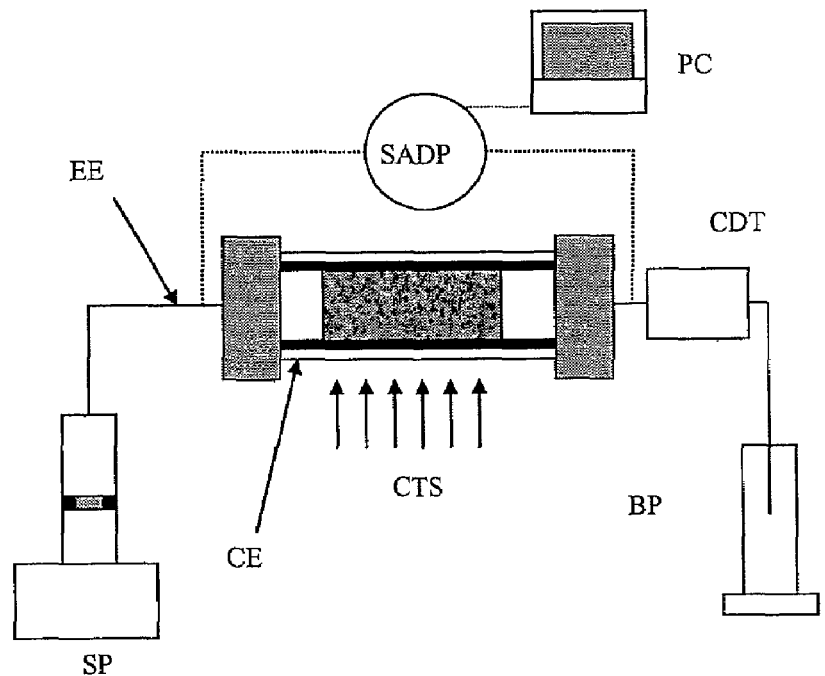
FIG. 1 illustrates an experimental device used to implement the method according to the invention to be implemented.

The necessary device is diagrammatically shown in FIG. 1. It mainly is a conventional sample holder cell (CE), provided with or without local pressure ports, a pumping system (SP) and a system (SADP) allowing automatic acquisition of the differential pressure (DP) connected to a computer (PC). One of the critical points is the use of a differential sensor suited to the permeability range of the sample tested. A conductimeter (CDT) can be positioned at the outlet to monitor the production of the injected fluid by adding a tracer thereto. A production buret (BP) can be added at the device outlet. The evolution of the fluid injected within the sample can be obtained through acquisition of X-ray measurements using a scanner (CTS) of CT-scanner type. The latter device can also allow acquisition of the 3D porosity map in the same environment. However, acquisition of these different types of measurement (conductimeter at the outlet and intermediate injected fluid concentration profiles) is not mandatory for analysis of the final data.

The sample mounted in the sample holder cell (CE) is initially saturated with a fluid of moderate viscosity (typically a brine) referred to as fluid 1 in the description hereafter. Its average absolute permeability is then measured by means of pump (SP) and of differential sensor (SADP) using Darcy's law. This permeability value is important because it is the value that dimensions the viscous miscible test according to the available material. For example, if a full-scale 10-bar differential sensor (SADP) is available, the injection rate of the high-viscosity fluid (referred to as fluid 2 hereafter) is calculated from this permeability value so that the induced differential pressure remains below the limit of the sensor.

Prior to starting injection of fluid 2, a dead volume is deliberately left in the inlet terminal part (EE) saturated with fluid 1 in place in the sample. This volume is very useful for measuring with precision the reference level of the differential pressure of the fluid in place under the experimental conditions (flow rate). Injection of fluid 2 occurs at an imposed flow rate, preferably using a pulseless pump to prevent artifacts in the pressure signal. Injection rates in a range of cubic centimeters per hour are typically used. The evolution of the differential pressure during the test is continuously measured, including during the initial period of emptying of the dead volume that precisely provides the reference level for the differential pressure of fluid 1. About two pore volumes of fluid 2 are generally injected to be sure to obtain a stabilized state in terms of differential pressure. The evolution of this pressure is continuously measured during the tests.

Once the viscous miscible test is complete, fluid 1 is reset in place in the sample by injection with the pump. The pressure evolution or (and) the conductimeter then allows evaluation of the good reset state of fluid 1. The displacement being here highly unstable, the heterogeneities are much more appreciable and it is generally necessary to inject a greater volume to find the initial state of fluid 1 again.

A second test is then carried out according to exactly the same procedures as the previous one, but injection is performed in the opposite direction.

Interpretation of the Results

1D Permeability Profile

Identification of the 1D permeability profile is based on the interpretation of the tests described above. The higher viscosity of fluid 2 in relation to displaced fluid 1 theoretically provides a favorable mobility ratio, which is translated into a piston type displacement in the sample. The displacement time of the front from the inlet to the outlet multiplied by the injection rate then corresponds to the pore volume of the sample studied. This calculation furthermore allows conversion of the experiment times into positions of the front of fluid 2 in the sample during injection.

Figure 2:
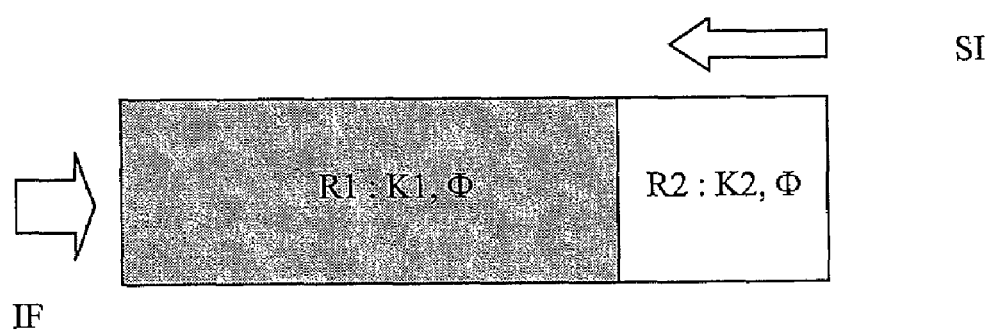
FIG. 2 shows the principle of the viscous miscible test with a "composite" heterogeneous sample.
Figure 3:
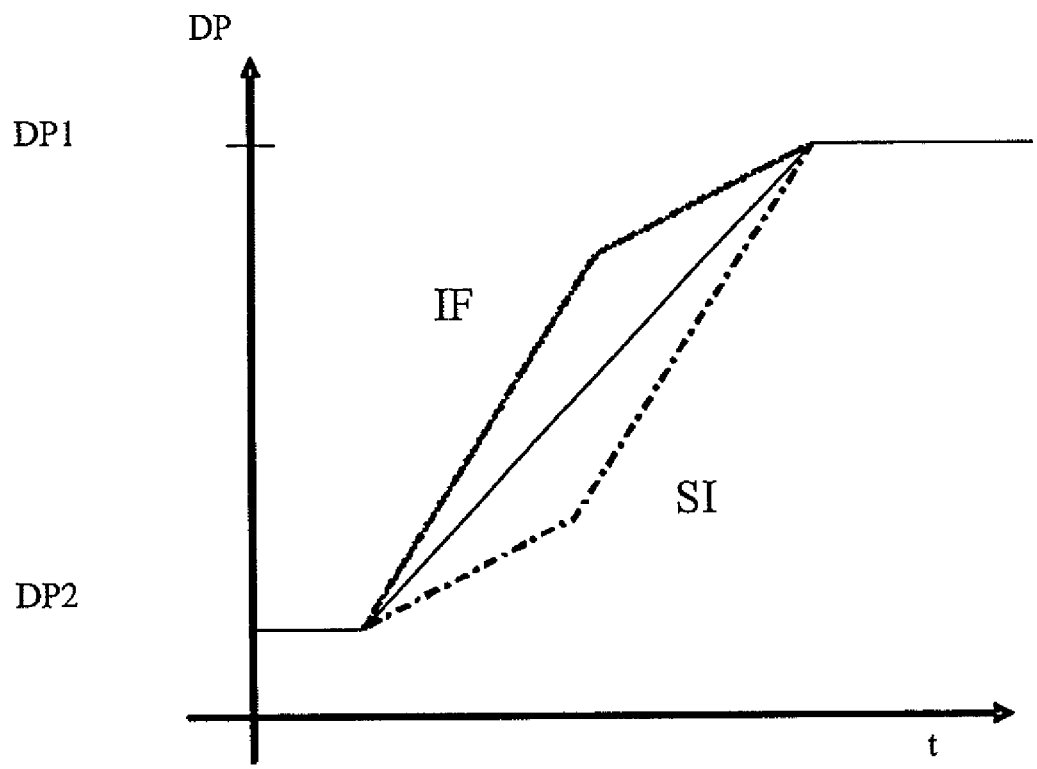
FIG. 3 shows the example of a differential pressure signal DP expected for the sample of FIG. 2.

Darcy's law implies that, for a perfectly homogeneous sample, the pressure evolution takes place in a strictly linear way with a single slope corresponding to the permeability value. For a composite sample with two different permeability regions, as illustrated in FIG. 2, two distinct linear parts are observed (FIG. 3). The composite sample of FIG. 2 is of a region R1 of permeability K1 lower than the permeability K2 of second region R2.

FIG. 3 illustrates an example of a differential pressure signal DP expected for the composite sample of FIG. 2. It should be noted that the permeability is lower in relation to the average in the first two thirds of the sample. In the direction of injection of the viscous miscible fluid (IF), the differential pressure curve DP is represented by a solid thick line. The first slope is more marked because it is the less permeable region (R1) through which the viscous front flows first. Then, a slight change of direction of the slope appears as the viscous front reaches the more permeable region R2. In this theoretical example, the break between the two slopes is reached for a time that is not symmetrical in relation to the two plateaux because region 1 is longer and the porosities ($\Phi$) are equal. The inverse test (SI) is represented by a curve of a broken line. This test leads to a completely symmetrical signature in terms of differential pressure. The first slope is the gentler, whereas the break occurs earlier, the plateau remaining the same. DP1 represents the differential pressure when the sample is entirely saturated with the injected fluid (fluid 2), and DP2 represents the differential pressure when the sample is entirely saturated with the fluid in place (fluid 1).

Differential pressure DP(t) is the pressure difference along the sample and, considering the nature of the test and depends on the time t. This differential pressure is the sum of the differential pressure in the part of the sample saturated with fluid 2 and of the differential pressure in the part of the sample saturated with fluid 1:

$$DP(t) = \int_0^{X_f} \frac{Q\mu_2}{AK(x)} dx + \int_{X_f}^{L} \frac{Q\mu_1}{AK(x)} dx \qquad (1)$$

Figure 4:
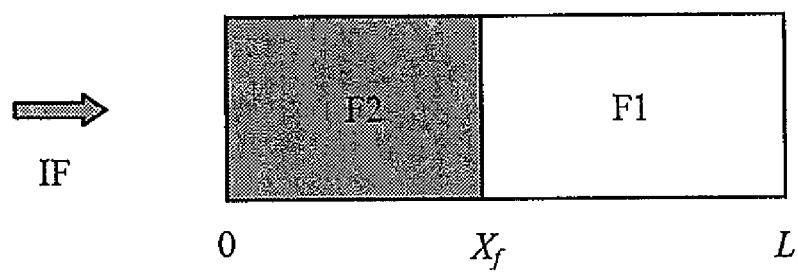
FIG. 4 illustrates the injection of fluid 2 (F2) into the sample initially saturated with fluid 1 (F1)

$X_f$ is the position of the front and depends on the time. L is the length of the sample. Q is the flow rate of the fluid through surface A, that is the surface of the sample perpendicular to the direction of flow. K is the permeability. The respective viscosities of fluids 1 and 2 are denoted by $\mu_1$ and $\mu_2$. FIG. 4 illustrates the injection of fluid 2 (F2) into the sample initially saturated with fluid 1 (F1). Fluid 2 is injected (IF), it saturates the sample between the longitudinal co-ordinates from 0 to $X_f$. Fluid 1 saturates the sample between the longitudinal co-ordinates from $X_f$ to L (length of the sample).

If reference is made to the Buckley-Leverett method (1942) developed for immiscible displacements, the position of the front is given by:

$$X_f = \frac{Q}{\phi A} t \qquad (2)$$

where $\phi$ is the porosity. The derivative of $X_f$ with respect to time thus is $Q/(\phi A)$.

It is deduced therefrom that the derivative of DP with respect to time thus is:

$$\frac{\partial DP}{\partial t} = \frac{Q^2}{A^2 \phi K(X_f)} (\mu_2 - \mu_1) \qquad (3)$$

Equation 2 gives the relation between the position of the front and time. It is then possible to estimate the permeability as a function of time:

$$K(t) = \frac{Q^2}{A^2 \phi} (\mu_2 - \mu_1) \frac{1}{\frac{\partial DP}{\partial t}} \qquad (4)$$

or, in an equivalent manner, the permeability along the sample. This first stage allows determination of the 1D permeability profile. A permeability value is representative of the average permeability over a slice of the sample, perpendicular to the direction of flow.

Figure 5:
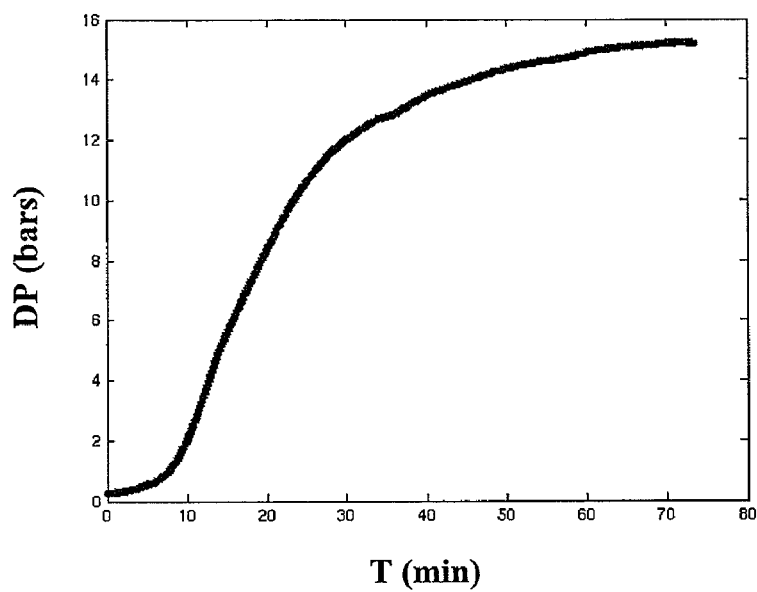
FIG. 5 shows a differential pressure curve (DP) measured as a function of time (T)
Figure 6:
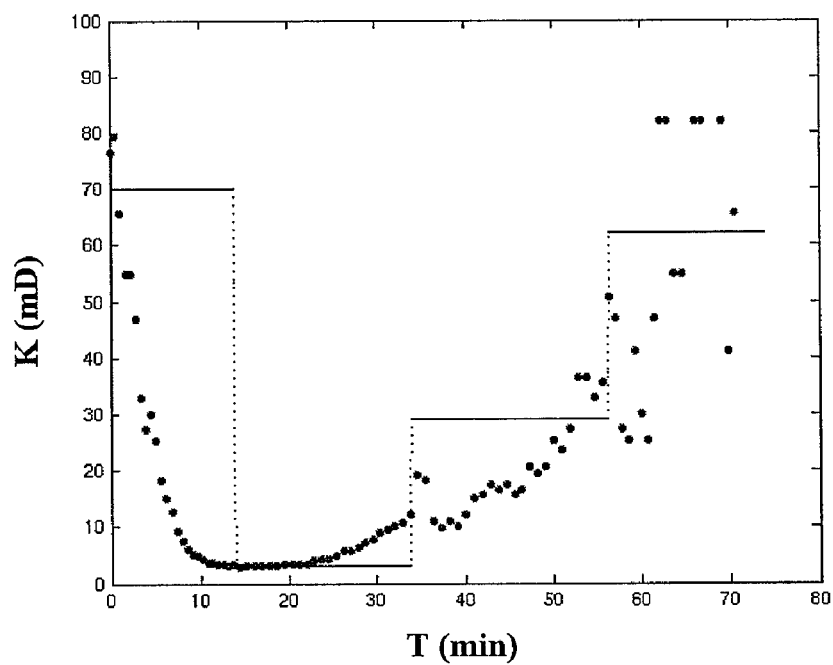
FIG. 6 illustrates a permeability profile (K) calculated as a function of time T and a theoretical permeability profile.
Figure 7:
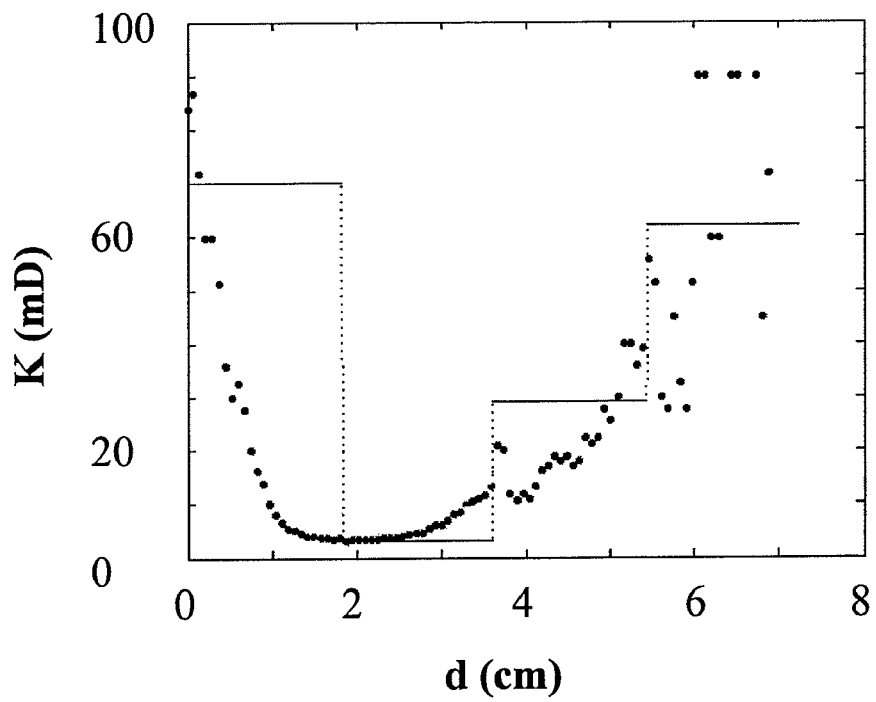
FIG. 7 shows a permeability profile calculated as a function of distance and a theoretical permeability profile.

In order to illustrate the first stage of the 1D permeability characterization process, a sample was constructed by laying end to end four different samples, quasi-homogeneous and of known effective permeabilities. The sample was initially saturated with a brine (30 g/l NaCl). Then glycerin was injected at a rate of 15 cm$^3$/h. The viscosity of the brine was 1.01 cP and that of the glycerin was 60 cP. The evolution of the differential pressure (DP) over the course of time (T) is shown in FIG. 5. Equation 4 allows to deduce therefrom the permeability profile (K) as a function of time (T), illustrated in FIG. 6. This profile is compared with the effective permeabilities measured for the four sample pieces. These pieces had been selected for their homogeneous character. The calculated profile reproduces the theoretical profile reasonably well. FIG. 7 shows the same profile as a function of the length (d) of the sample. In FIG. 6, the dots represent the calculated permeability profile as a function of time, and the black curve represents the theoretical permeability profile. Similarly, in FIG. 7, the dots represent the calculated permeability profile as a function of the distance, and the black curve represents the theoretical permeability profile.

3D Permeability Map

The interpretation principle is based on a combination of dynamic results (1D permeability profile) with static results (3D porosity map). In fact, assuming that there is a porosity/permeability law (K($\phi$)) valid on the scale of the discretization selected for the 3D porosity map, it is then possible to calculate an a priori 3D permeability map. By averaging the permeability at the various slices (parallel calculation), we obtain information that is directly comparable with the measured 1D permeability profile directly by interpretation of dynamic tests. The goal is then to optimize law K($\phi$) so as to obtain the best agreement possible between the two profiles.

Figure 8:
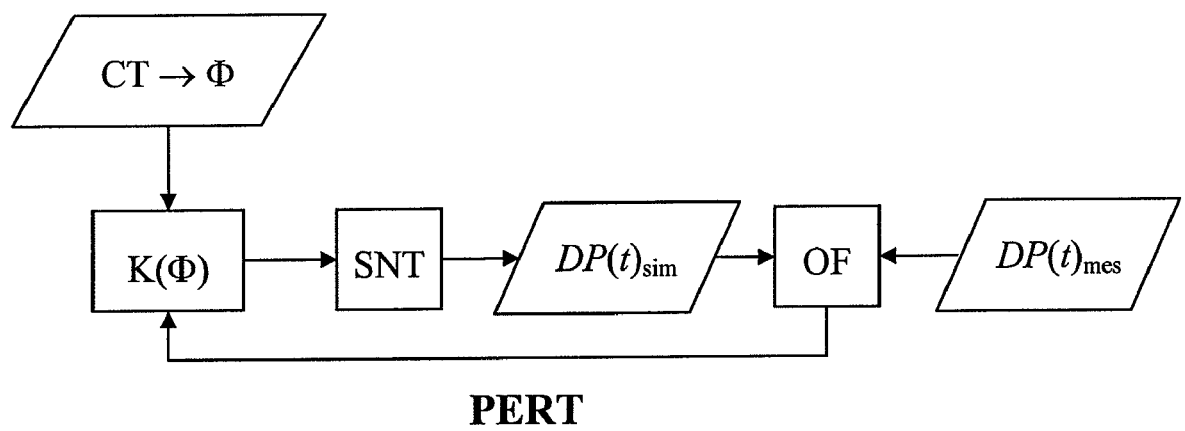
FIG. 8 describes the determination of a 3D permeability map by calibrating the differential pressures.

FIG. 8 illustrates the various stages followed to obtain a 3D permeability map coherent with the available data, that is the 3D porosity map and the differential pressure measured over the course of time.

1) First a 3D permeability map (K($\Phi$)) is constructed from the 3D porosity map (3D porosity map $\Phi$ deduced from data CT). A stochastic context can be chosen and a co-simulation process used in which case the permeability map depends on a seed and it is correlated with the porosity. A deterministic relation can also be used between the porosity and the permeability. For example, law $K(\phi)$ can take the form as follows: $K = \alpha(\phi - \phi_0)^\beta$ where:
α is a prefactor;
$\phi_0$ the residual porosity, that is a porosity value for which the flow can no longer take place; and
β an exponent expressing the evolution of the permeability as a function of the effective porosity.

Within the context of the study of a porous medium having a more complex structure (bimodal for example), it is possible to introduce two laws $K1(\phi)$, $K2(\phi)$, as well as a porosity threshold value $\phi_c$ allowing to distinguish the cells where each law has to be applied.

2) The 3D permeability map being known, the viscous miscible test (SNT) is numerically simulated. The simulation results, that is the simulated differential pressure $(DP(t)_{sim})$, are then compared with the differential pressure measured over the course of time $(DP(t)_{mes})$. Therefrom the value of an objective function (OF) is deduced. Objective function OF measures the difference between the real data and the simulated corresponding responses. It is also possible to express this function differently. For example, it could measure the difference between the 1D permeability profile deduced from the pressure data and the 1D permeability profile deduced from the simulated pressures.

3) The last stage perturbs (PERT) the parameters of the problem in order to determine a 3D permeability map that minimizes the objective function, that is minimizing the difference between the measured differential pressure and the corresponding digital signal.

In case of a co-simulation, the permeability map is modified by applying for example the gradual deformation method. In case of a deterministic relation, the parameters involved in the law are modified, for example α, $\phi_0$ and β.

Figure 9:
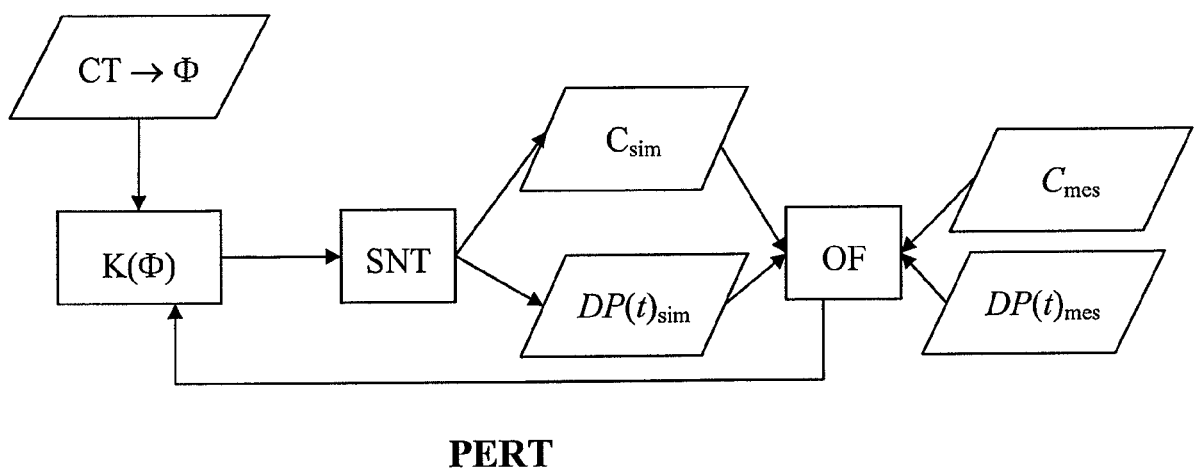
FIG. 9 describes the determination of a 3D permeability map by calibrating the differential pressures and the concentration data.

This calibration process can be enriched by concentration measurements (C). In fact, when the experiment is carried out with a scanner, it is possible to obtain a concentration profile or 3D concentration maps at different times $(C_{mes})$ from X-ray measurements (Maloney and Wegener, 2000). These data can be integrated in the objective function to be compared with the equivalent simulated responses $C_{sim}$ (FIG. 9).

The potential applications of this method are significant, in particular as regards the characterization of heterogeneous porous media such as vuggy media for example, or porous media subjected to reactive flows (following $CO_2$ injection or acid well stimulation operations for example).

The invention claimed is:

1. A method of determining a 3D distribution of absolute permeability in a heterogeneous sample to a flow of fluid therein, comprising:

providing a 3D porosity map obtained from the sample;
performing a static measurement of the 3D porosity map of the sample;
performing at least one viscous miscible displacement test during which an evolution of differential pressure is determined on either side of the sample;
determining a 1D absolute permeability profile along the sample using evolution of the differential pressure;
constructing a 3D permeability map from the 3D porosity map;
estimating a simulated differential pressure by simulating numerically a viscous miscible test from the 3D permeability map and the 1D absolute permeability profile; and
determining the 3D distribution of the absolute permeability of the heterogeneous sample by modifying at least once the 3D permeability map to minimize a difference between the simulated differential pressure and differential pressure measured over of time.

2. A method of determining the 3D distribution of the absolute permeability of a heterogeneous sample as claimed in claim 1, wherein the 3D porosity map is determined from non-destructive static measurements.

3. A method of determining the 3D distribution of the absolute permeability of a heterogeneous sample as claimed in claim 1, wherein the 3D porosity map is determined from X-ray measurements using fluids of different densities saturating the sample.

4. A method of determining the 3D distribution of the absolute permeability of a heterogeneous sample as claimed in claim 1, wherein the 3D permeability map is determined from co-simulations.

5. A method of determining the 3D distribution of the absolute permeability of a heterogeneous sample as claimed in claim 1, wherein the 3D permeability map is determined from at least one deterministic relation between porosity and permeability.

6. A method of determining the 3D distribution of the absolute permeability of a heterogeneous sample as claimed in claim 1, wherein a concentration profile or 3D concentration maps are determined at different times and compared with equivalent simulated responses.

7. A method of determining the 3D distribution of the absolute permeability of a heterogeneous sample as claimed in claim 2, wherein the 3D porosity map is determined from nuclear magnetic resonance measurements.

8. A method of determining the 3D distribution of the absolute permeability of a heterogeneous sample as claimed in claim 4, wherein the 3D permeability map is modified by applying a gradual deformation method.

* * * * *